United States Patent [19]

Manghisi et al.

[11] Patent Number: 4,761,422

[45] Date of Patent: Aug. 2, 1988

[54] (2-AMINO-4-ARYL-THIAZOLE-5-YL)E-THANOLS AND THEIR DERIVATIVES HAVING DIURETIC ACTIVITY AND METHODS FOR PREPARING THE SAME

[75] Inventors: Elso Manghisi, Monza; Aldo Salimbeni, Sesto San Giovanni, both of Italy

[73] Assignee: Lusofarmaco Istituto Lusofarmaco d'Italia SpA, Milan, Italy

[21] Appl. No.: 932,929

[22] Filed: Nov. 19, 1986

[51] Int. Cl.$^4$ ............... C07D 277/40; C07D 277/42; A61K 31/425
[52] U.S. Cl. ..................... 514/370; 548/193; 548/194
[58] Field of Search ............... 548/193, 194; 514/370

[56] References Cited

PUBLICATIONS

March, Advanced Organic Chemistry, pp. 346, 347 (1985).

Primary Examiner—Robert Gerstl
Attorney, Agent, or Firm—Wolf, Greenfield & Sacks

[57] ABSTRACT

This invention relates to a series of thiazole derivatives having the general formula

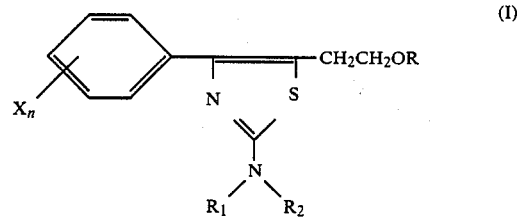

The compounds of the invention have an interesting diuretic activity and low toxicity.

5 Claims, No Drawings

(2-AMINO-4-ARYL-THIAZOLE-5-YL)ETHANOLS AND THEIR DERIVATIVES HAVING DIURETIC ACTIVITY AND METHODS FOR PREPARING THE SAME

SUMMARY OF THE INVENTION

This invention relates to a series of thiazole derivatives of the general formula (I)

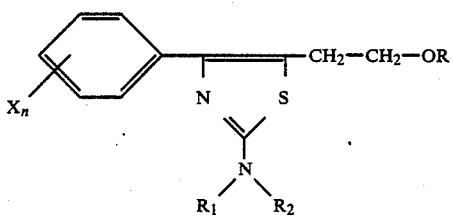

wherein:
R is a hydrogen atom or an acyl radical of a carbamic, allophanic, or a $C_1$-$C_4$ aliphatic or aromatic acid, possibly substituted by halogen atoms or alkoxy groups,
$R_1$ and $R_2$, which can be equal or different, are a hydrogen atom, a lower alkyl group with 1 to 4 carbon atoms, a phenyl group, possibly substituted in the aromatic ring by one or more halogen atoms selected from fluorine, chlorine, bromine and X is a hydrogen atom, a halogen atom selected from fluorine, chlorine and bromine, a hydroxy group, a lower alkoxy or a sulfonamide group, and n is 1 to 3.

This invention also relates to salts of the compounds of formula I with pharmaceutically acceptable acids such as hydrochloric, hydrobromic, sulfuric acid, etc. as well as organic acids like maleic, fumaric, malic, tartaric, citric acids, etc.

The invention also relates to methods for preparing compounds of the general formula I.

DETAILED DESCRIPTION OF THE PREFERRED EMBODIMENT

The preparation of the compounds of the general formula I, wherein R=H, can be carried out by reducing by catalytic or chemical methods a free or esterified carboxylic function present in thiazole derivatives of the general formula II

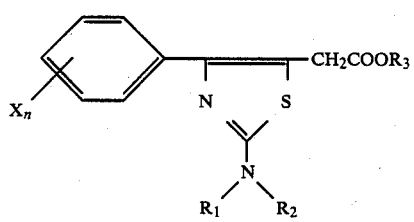

wherein $R_1$, $R_2$, X have the meanings set forth above, while $R_3$ can be hydrogen or a methyl or ethyl group.

In the reduction reaction an organometal compound is preferably used, such as $LiAlH_4$ or $NaAlH_2(OCH_2CH_2OCH_3)_2$, by carrying it out in a non polar solvent such as ethyl ether or tetrahydrofuran at the boiling point of the solvent.

The thiazole derivatives of the general formula II, used herein as starting materials, can be prepared as disclosed in the U.S. Pat. No. 3,933,838 pertaining to the same Applicant of the present.

The preparation of the compounds of the general formula I, wherein R=$CONH_2$ or R=$CONHCONH_2$ can be carried out by reacting the compounds of formula (I) obtained before, wherein R=H, with alkali metal (such as sodium or potassium) cyanates in the presence of acids or by reaction with phosgene and then with ammonia. The reaction with alkali metal cyanates is however preferred. It is generally carried out with an excess of the reagent (2 to 4 moles) in a non polar solvent (such as chloroform, methylene chloride, etc) in the presence of an organic acid (e.g. $CF_3COOH$) or inorganic acid (e.g. HCl) at room temperature.

The preparation of the compounds of the general formula (I), wherein R is an acyl radical of an aliphatic or aromatic acid can be carried out by reacting a compound (I), wherein R=H, with a reactive derivative of the corresponding acid (such as chloride, bromide, anhydride, and so forth). Such a reaction is preferably carried out in a non polar solvent such as benzene, toluene, etc) in the presence of a base (e.g. triethylamine, pyridine, etc).

The compounds of the present invention have revealed, when subjected to a pharmacological screening, to be in possession of an interesting diuretic activity and low toxicity.

The diuretic activity has been determined according to the method by G. B. Fregnan et al., *Gazzetta Medica Italiana* 128, 384 (1969).

In the Table given hereinbelow the pharmacological data of some of the compounds according to the invention in comparison with thienyl acid are set forth.

The compounds according to the invention can be usefully employed in the human therapy as diuretic and antihypertensive agents. They can be administered orally or by injection, in the form of suitable pharmaceutical formulations in solid, liquid or suspension form (tablets, capsules, vials, syrups, etc).

The examples which follow illustrate the invention without limiting the same. The identity of the substances and their purity have been ascertained by elemental analysis (C, H, N) and IR, NMR and UV spectroscopy.

EXAMPLE 1

2-[2-amino-4-(p-chlorophenyl)thiazole-5-yl]ethanol (LR 409)

To a suspension of 7 g of $LiAlH_4$ in 1,200 ml of anhydrous ethyl ether 40 g of ethyl[2-amino-4-(p-chlorophenyl)-thiazole-5-yl-methyl]carboxylate dissolved in 500 L ml of anhydrous ethyl ether are portionwise added under stirring. Once the addition is completed heating to reflux is performed for 3 hours. After cooling, the excess of $LiAlH_4$ is cautiously destroyed with $H_2O$. The inorganic salts are filtered off and the solution is brought to dryness.

The residue is crystallized from $CHCl_3$: 22 g, melting point 111°–113° C.

A salt with maleic acid is prepared by mixing equimolar amounts of base and acid dissolved in isopropyl alcohol; melting point 177°–179° C. (from EtOH).

In an analogous manner the following compounds are prepared:

(1) 2-[2-methylamino-4-(p-chlorophenyl)thiazole-5-yl]ethanol (LR 861) melting point 108°–110° C. (from benzene)
(2) 2-[2-diethylamino-4-(p-chlorophenyl)thiazole-5-yl]ethanol (LR 440) melting point 91°–92° C. (from benzene)
(3) 2-[2-phenylamino-4-(p-chlorophenyl)thiazole-5-yl]ethanol (LR 497) melting point 157°–159° C. (from EtOH)

EXAMPLE 2

2-[2-amino-4-(p-chlorophenyl)thiazole-5-yl]ethanol carbamate (LR 890)

To a solution of 35 g of 2-[2-amino-4-(p-chlorophenyl)thiazole-5-yl]ethanol in 1,600 cc of $CH_2Cl_2$, 22.3 g of KCNO are added all at once and then 31 cc of $CF_3COOH$ are dropwise added. Once the addition is complete the reaction is left to proceed for 48 h at room temperature. The precipitated solid is filtered, washed with $H_2O$ and then crystallized from isopropyl alcohol: 5.6 g, melting point 215°–216° C.

In an analogous manner the following compounds were prepared:
(1) 2-[2-methylamino-4-(p-chlorophenyl)thiazole-5-yl]ethanol carbamate M.P. 183°–185° C. (from iso-PrOH) (LR 892)
2-[2-diethylamino-4-(p-chlorophenyl)thiazole-5-yl]ethanol carbamate M.P. 138°–139° C. (from benzene) (LR 525)

EXAMPLE 3

2-[2-diethylamino-4-(p-chlorophenyl)thiazol-5-yl]ethanol allophanate

Gaseous HCl is bubbled for 20 minutes into a solution of 30 g of 2-[2-diethylamino-4-(p-chlorophenyl)thiazol-5-yl]ethanol in 1 l of dioxane. Then 31.5 g of NaCNO are added portion wise. When the addition is complete stirring is continued for 24 h. The solid is filtered off and the solution is brought to dryness. The residue is dissolved in $CHCl_3$ and the resulting solution is repeatedly washed with $H_2O$. It is dried on $Na_2SO_4$ and the solvent is removed under vacuum. Crystallization is carried out from isopropyl alcohol: 24.1 g, M.P. 194°–196° C.

EXAMPLE 4

Pharmaceutical formulation: tablets

| | |
|---|---|
| 2-[2-diethylamino-4-(p-chlorophenyl)thiazole-5-yl]ethanol carbamate | 15 mg |
| Vehicle qs | 75 mg |

| Designa- | Compound | | | | Diuretic activity in rat | Acute toxicity in rat |
|---|---|---|---|---|---|---|
| tion | $R_1$ | $R_2$ | R | X | $DA_{200}$ (mg/kg os)* | $DL_{50}$ (mg/kg ip) |
| LR 409 | H | H | H | Cl | 30 | 280 |
| LR 440 | $C_2H_5$ | $C_2H_5$ | H | Cl | 100 | >1000 |
| LR 861 | H | $CH_3$ | H | Cl | 100 | 750 |
| LR 890 | H | H | $CONH_2$ | Cl | 3 | >2000 |
| LR 892 | H | $CH_3$ | $CONH_2$ | Cl | 10 | >1000 |
| LR 525 | $C_2H_5$ | $C_2H_5$ | $CONH_2$ | Cl | 3 | >2000 |
| LR 856 | H | H | $CONHCONH_2$ | Cl | 5 | >1000 |
| Thienyl acid | | | | | 100 | 350 |

*Dosage causing doubling of the urinary volume

We claim:
1. Thiazole derivatives of the general formula I

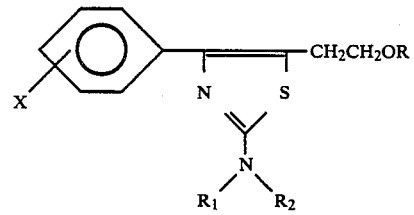

wherein:
R is a hydrogen atom or an acyl radical of a carbamic or allophanic acid, $R_1$ is a hydrogen atom or a lower alkyl with 1 to 4 carbon atom, $R_2$ is a hydrogen atom, a lower alkyl with 1 to 4 carbon atoms or a phenyl group, X is a hydrogen atom or a halogen atom selected from fluorine, chlorine and bromine and the pharmaceutically acceptable salts thereof.

2. Thiazole derivative according to claim 1 wherein said derivative comprises
2-[2-diethylamino-4-(p-chlorophenyl)thiazole-5yl]ethanol carbamate and the pharmaceutically acceptable salts thereof.

3. Thiazole derivative according to claim 1 wherein said derivative comprises 2-[2-amino-4-(p-chlorophenyl)thiazol-5yl]ethanol carbamate and the pharmaceutically acceptable salts thereof.

4. Thiazole derivatives according to claim 1 wherein said derivative comprises 2-[2-amino-4-(p-chlorophenyl)thiazol-5-yl]ethanol allophanate and the pharmaceutically acceptable salts thereof.

5. Pharmaceutical composition having diuretic activity which comprises an effective amount of a compound according to claim 1 and a pharmaceutical carrier therefor.

* * * * *